United States Patent [19]

Stokke

[11] 4,165,257
[45] Aug. 21, 1979

[54] BIOPOLYMER FILTERABILITY IMPROVEMENT BY CAUSTIC-ENZYME TREATMENT

[75] Inventor: Olaf M. Stokke, Ponca City, Okla.

[73] Assignee: Continental Oil Company, Ponca City, Okla.

[21] Appl. No.: 886,021

[22] Filed: Mar. 13, 1978

[51] Int. Cl.$^2$ .................... C12D 13/04; E21B 43/22
[52] U.S. Cl. .................... 435/262; 166/246; 252/8.55 D
[58] Field of Search .............. 195/2, 4, 7, 31 P, 3 R, 195/3 H; 166/246; 252/8.55 D

[56] References Cited

U.S. PATENT DOCUMENTS

| 3,964,972 | 6/1976 | Patton | 195/31 R |
| 4,010,071 | 3/1977 | Colegrove | 195/7 |
| 4,119,491 | 10/1978 | Wellington | 195/7 |

*Primary Examiner*—Lionel M. Shapiro
*Attorney, Agent, or Firm*—Cortlan R. Schupbach, Jr.

[57] ABSTRACT

In an enhanced recovery process involving flooding of subterranean formations with aqueous mixtures of biopolymers, filterability of the biopolymer is synergistically enhanced by treatment with ESPERASE® enzyme at a pH range of 12.5 to 13.0. The range is narrow and exclusive since pHs as high as 12.1 give poor results. The biopolymer can be any one containing debris which must be reduced by the enzyme.

4 Claims, No Drawings

BIOPOLYMER FILTERABILITY IMPROVEMENT BY CAUSTIC-ENZYME TREATMENT

This invention relates to an enhanced recovery process involving flooding of aqueous mixtures of biopolymers into a subterranean formation to recover hydrocarbons therefrom. More specifically this invention deals with a method for improving the filterability of the biopolymer prior to injection into the subterranean formation by treatment with a specific enzyme at a pH range of 12.5 to 13.0.

It has been found that biopolysaccharide, a biologically derived polymer, in water solution has excellent low mobility properties which make it desirable for a drive fluid to push enhanced recovery chemical banks through subterranean formations containing hydrocarbons to enhance recovery. The polymer prevents fingering or channeling of water through the chemically enhanced recovery bank thereby greatly increasing hydrocarbon recovery from the formation. Polysaccharides are frequently referred to as xanthum gums and are sold by various companies such as the Kelco Company, subsidiary of Merck Inc., General Foods, and others.

However, while a biopolysaccharide polymer is highly desirable from a hydrocarbon recovery standpoint, the biopolysaccharide polymer causes considerable operating problems in actual practice. Initially, the polymer must be filtered in order to be in condition for injection into the formation. Filtration removes gels and solid debris from the polymer solution. If filtration is not carried out prior to injection, the large amounts of fluid moving through a limited face of the formation quickly clogs the formation pores, much as a filter is clogged when removing debris from a fluid. At this point the well is unuseable and must be refractured, redrilled, or treated with acid or other treatment well known to the art.

Typically, attempts to filter the xanthum gum resulted in quickly blocking off flow through the filter used. Difficulty in filtering causes operating problems, particularly if filtration cannot keep up with the injection rate which in many actual field formations is quite high. In addition, with the frequent backwash required, a great deal of the operator's time is devoted to backwashing and repairing the filter, all of which greatly increases cost of operation. This is true even when diatomaceous earth filters are used, which are more efficient in this operation than most filters.

It would therefore be desirable to provide a method for increasing the filterability of the biopolysaccharide polymers used in enhanced recovery processes involving flooding subterranean formations to remove hydrocarbons therefrom.

It is therefore an object of the present invention to provide an enhanced recovery process involving flooding of aqueous mixtures of biopolymers whereby the filterability of the biopolymer is synergistically enhanced. Other objects will become apparent to those skilled in this art as the description proceeds.

It has now been discovered according to the present invention that when an excess of caustic is added at levels well above the levels normally recommended for use with an enzyme specified for use in basic solutions, beneficial synergistic effects result from the higher pH, whereby the caustic or enzyme or both are more effective in destroying proteinaceous debris residual which is in the polymer from the fermentation process, thereby greatly reducing or eliminating the need for conditioning by filtration.

The discovery of the instant invention was made through the use of defective equipment. A sample of ESPERASE® (trademark of and sold by NOVO Terapeutisk Laboratorium A.S., hereinafter NOVO) was found to effect an improvement in softened brine at pH 12.1, but not an unsoftened brine at 12.1. This was surprising, as the producer had not recommended useage at pH above 11. Thus the synergistic effect appeared to have occurred. When the samples were rechecked it was found that due to a malfunctioning electrode the softened brine was actually at pH 12.75 while the unsoftened was at pH 12.1. Subsequent studies found that the high pH of 12.75 was required for effective results. The pH and not the hardness was the important variable.

The prior art has previously recognized the use of enzymes and caustic solutions. The brochure from Novo Enzymes discloses that ESPERASE® enzyme, useful in the instant invention, is a proteolytic enzyme preparation obtained from a strain of bacillus. ESPERASE® enzyme is disclosed to hydrolyze all proteinaceous substances normally encountered in laundry. This enzyme is more completely described with reference to U.S. Pat. Nos. 3,723,250 and 3,674,643.

Society of Professional Engineers (SPE) paper 5372 discloses that treatment of xantham gum biopolymers with certain enzymes breaks down cell debris and improves injectivity. This reference discloses pH ranges of 6 to 11 with an optimum of 8–10. *Society of Professional Engineers* (SPE) paper 5099 discloses that injectivity problems with xantham gums are believed to be due to cell residue or microgels. Clarification of the biopolymer solutions is disclosed to be affected by the use of alkylene protease enzymes such as ALKALASE® (trademark of and sold by NOVO) or MAXAZYME® (trademark of and sold by Enzyme Industries).

U.S. Pat. No. 4,010,071 discloses that aqueous suspension of xanthum gums are clarified by treatment with protease enzyme such as the alkaline protease produced by bacillus microorganisms. A problem aggravated by degradation of cellular residue is plugging of oil well flooding operations. PH levels for use of the enzymes is disclosed to be in the range of 7 to 12. Example 14 discloses the use of ESPERASE® alkaline protease enzyme produced by Novo Industries, subject of the instant application, to clearify xanthum gum solution. Other similar enzymes are disclosed.

The publication *Maxitase* of the Royal Netherlands Fermentation Industry is limited, disclosing an activity range of pH 7 to 11 for MAXITASE® proteolytic enzyme.

U.S. Pat. No. 3,622,458 discloses an alkaline protease derived from a bacillus microbe having declining activity to pHs as high as 12.7.

However, none of these references have taught or disclosed the enhanced results found in the synergistic interaction of a particular enzyme sold under the tradename ESPERASE® by Novo Enzyme Corporation. The manufacturer in commercial brochures recommends a pH range of between 8 and 12 for this material. Early studies indicated that the material was ineffective at pHs of 12.1 yet surprisingly became highly active at pH 12.5 and continued to be highly active through a pH of 13.0.

Thus the instant invention relates to an improved hydrocarbon recovery process wherein subterranean petroliferous formations are flooded with aqueous mixtures of biopolymers to increase hydrocarbon recovery, said biopolymer being treated with bacillus produced enzyme, tradenamed ESPERASE ®, to solubilize cell debris prior to filtration, the improvement comprising treating the polymer prior to filtration and use in a petroliferous formation with ESPERASE ® enzyme at a pH of 12.5 to 13.0 to improve filterability, then filtering prior to use if necessary.

The method for obtaining the caustic solution can be by any means well known in the art, such as by the addition of sodium hydroxide, potassium hydroxide, and so forth. Normally the treatment is carried out at a temperature of from about 76° F. to about 120° F. but most preferred is at a temperature of from about 100° F. to about 120° F. The enzyme is normally added to the biopolymer at levels of from about 2½% to about 10% by weight based upon the weight of the biopolymer. Additions of enzyme above levels effective to decrease the proteinaceous material contained in the polymer are wasteful and no additional benefit is seen.

Filtration following the treatment of the enzyme may or may not be necessary depending upon the particular formation and the particular starting biopolymer chosen. However, in most cases some filtration will be necessary, but filter plugging will be greatly reduced because of the decrease of debris in the biopolymer because of the treatment of the instant invention. Such filtration can be by any method well known to those skilled in the art but normally will be by methods such as diatomaceous earth (DE) filters.

The invention is more concretely described with reference to the examples below wherein all parts and percentages are by weight unless otherwise specified. The examples are illustrative of the instant invention and do not limit it.

Biopolymers used were Xanflood, Spec 12 and SS 4000 all trademarks of and sold by the Kelco Company, subsidiaries of Merck, Inc. Comparative filtration tests were carried out using distilled water, synthetic soft Sundance brine (SSD) at about 0.4 weight percent total salts and SSD enriched to 1 weight percent total salts with sodium chloride (SSD→1%). The preceeding waters were adjusted to the appropriate pH with sodium hydroxide for use as polymer hydration brines. Hydration brine was preheated to 110° F. before the enzyme and polymer were added. The dry enzyme as received from the manufacturer was added to the hydration brine ahead of the polymer at 5% of the polymer weight. Half of the polymer concentrate was sheared immediately through a spray nozzle (3 times) at a pressure drop of 500 pounds per square inch gauge (psig) per pass. The sheared and unsheared polymer concentrate samples were then aged for 4 hours in a constant temperature bath of 110° F. All samples were so aged.

Dilute part per million solutions were made with enriched Sundance brine (SSD→1%) at a pH of 12.1 to simulate field dilution brine. These dilute samples were evaluated for filterability using standard laboratory test procedures with 0.8 micron Millipore ®, filters (trademark of Millipore Corp) and diatomaceous earth. Viscosities were measured before and after filtration with a Brookfield Underwriter's Laboratory adaptor viscometer at a spindle speed of 30 rpm and a temperature of 115° F.

The ratio of the time necessary for the last 50 milliliters (mls) of 500 ml to flow through a filter at constant pressure relative to the time for the first 50 mls to flow provides a convenient qualitative measure of the ease with which a solution can be filtered and its tendency for plugging. Normal criteria for fluids flow ratio, that is the time for the last 50 of 500 mls throughput relative to the first 50 ml be no greater than 2.0. A filter is defined as plugged when a time of more than 200 seconds is required to flow an increment of 50 ml. Various tests were carried out using for hydration distilled water or digested Sundance brine at room temperature pHs ranging from 12.1 to 13, both with and without enzyme addition, and with and without shearing the concentrated slurry. The results are shown in Table 1.

TABLE 1

SUMMARY OF CAUSTIC-ENZYME TESTS

|      | Hydration Brine |      |        | Sheared Conc. | Dilute Feed cps | .8u Millipore ® on Feed |  |  | .8u Millipore ® on d.e. Filtrate |  |  |
|------|-----------------|------|--------|---------------|-----------------|-------------------------|--|--|----------------------------------|--|--|
|      |                 |      |        |               |                 | Flow in Sec. |  | | Flow in sec. | | |
| Test | Salinity | pH | Enzyme | | | 0–50 mls | 450–500 mls | Filtrate cps | 0–50 mls | 450–500 mls | Filtrate cps |
| 1 | Dist. Water | 12.1 | No  | No  | 2.44 | 12 | P @ 95 ml  | 2.44 | 11 | 17 | 2.34 |
| 2 | Dist. Water | 12.1 | No  | Yes | 2.24 | 12 | P @ 121 ml | 2.24 | 9  | 15 | 2.19 |
| 3 | Dist. Water | 12.1 | Yes | No  | 2.44 | 11 | 97         | 2.44 | 10 | 15 | 2.40 |
| 4 | Dist. Water | 12.1 | Yes | Yes | 2.20 | 11 | P @ 209 ml | 2.20 | —  | —  | —    |
| 5 | SSD | 12.5 | Yes | No  | 2.38 | 9  | 17         | 2.38 | 10 | 14 | 234  |
| 6 | SSD | 12.5 | Yes | Yes | 2.10 | 9  | 13         | 2.08 | 9  | 15 | 202  |
| 7 | SSD | 12.8 | Yes | No  | 2.32 | 10 | 20         | 2.32 | 9  | 16 | 2.28 |
| 8 | SSD | 12.8 | Yes | Yes | 2.18 | 9  | 14         | 2.18 | 9  | 14 | 2.16 |
| 9 | SSD | 12.8 | No  | No  | 2.42 | 11 | P @ 159 ml | 2.42 | 10 | 30 | 2.30 |
| 10 | SSD | 12.8 | No | Yes | 2.18 | 10 | P @ 245 ml | 2.18 | 10 | 15 | 2.06 |
| 11 | SSD | 13.0 | Yes | No  | 2.34 | 9  | 30         | 2.34 | 10 | 20 | 2.32 |
| 12 | SSD | 13.0 | Yes | Yes | 2.28 | 9  | 15         | 2.28 | 9  | 14 | 2.16 |

P - designated plugged filter

In all cases the enzyme used was ESPERASE P ®.

Caustic enzyme diatomaceous earth precoat tests were then carried out on four additional samples showing flow time through diatomaceous earth precoats containing no body feed at a pressure differential of 10 pounds per square inch. Example 15 shows as plugged since more than 200 seconds were required to flow 50 ml. Results are shown in Table II.

Table II

CAUSTIC-ENZYME D.E. PRECOAT TESTS
500 ppm Polymer Solutions

| Test | Polymer Hydration Brine | Enzyme | Sheared | Dilution Brine | pH | Flow Time Through D.E. Precoat*, sec, 0-50 mls 950-1000mls |
|---|---|---|---|---|---|---|
| 13 | SSD→1%, pH 12.8 | Yes | Yes | SSD→1%, 12.1 | 11 | 16 |
| 14 | SSD→1%, pH 12.8 | Yes | Yes | SSD→1%, 12.1 | 10 | 15 |
| 15 | SSD→1%, pH 12.1 | No | Yes | SSD→1%, 12.1 | 11 | P @ 900 mls |
| 16 | SSD→1%, pH 12.1 | No | Yes | SSD→1%, 12.1 | 12 | 113 |

Table III shows the effect of enzyme concentration on Kelco's Xanflood ® polymer with ESPERASE ® enzyme at a pH of 12.8. The diatomaceous earth filtration was made on a precoat only with no body feed. Filtrations were carried out at room temperature with a pressure differential of 10 pounds per square inch gauge. Viscosities were determined at 115° F. and 30 rpm as previously described.

TABLE III

EFFECT OF ENZYME CONCENTRATION

| Polymer Concentrate | | | Dilute Feed Vis, cps | 0.8 u Millipore ® on Feed | | | | d.e. Precoat on Feed | | | |
|---|---|---|---|---|---|---|---|---|---|---|---|
| | | | | Flow Time, Sec | | | | Flow Time, Sec | | | |
| Enzyme | | | | 0-50 | 450-500 | Flow | Vis, filtrate | 0-50 | 950-1,000 | Flow | Filtrate |
| ppm | wt % Poly. | Sheared | | mls | mls | Ratio | Vis, cps | mls | mls | Ratio | Vis, cps |
| 5,000 | 5 | Yes | 2.14 | 9 | 15 | 1.67 | | 9 | 15 | | |
| 5,000 | 5 | Yes | | 8 | 13 | 1.62 | | 11 | 16 | 1.45 | |
| 5,000 | 5 | Yes | | 8 | 11 | 1.38 | | 11 | 15 | 1.36 | |
| 5,000 | 3.3 | Yes | | 9 | 15 | 1.67 | | 11 | 16 | 1.45 | |
| 5,000 | 10 | Yes | 2.22 | 9 | 14 | 1.56 | 2.26 | 11 | 18 | | 1.26 |

Thus it can be seen that the sensitivity of the enzyme treatment shows little difference based on enzyme concentrations so long as other factors are the same. Marginally better results were obtained when polymer was hydrated to a concentration of 5,000 parts per million rather than 10,000 parts per million. Decreasing the enzyme concentration from 5 to 3.3 weight percent of the polymer weight or increasing it to 10 weight percent had no significant effect on the filterability. Increasing the age time at 110° F. of a 5,000 ppm polymer concentrate with 250 ppm enzyme from 4 to 24 hours had little effect. All the data shows that a pH of 12.5 to 13.0 in the hydration brine was required for the enzyme to be effective. A lower pH of 12.1 with enzyme or a high pH of 12.8 without enzyme was not effective. Test 3 of Table I did not plug filters, but had a very low flow rate compared to the instant method. PH ranges between 12.5 and 13 also show low flow rates.

Softening both the hydration and dilution brines could assist in the destruction of the proteinaceous material. In addition, filterability can be improved by surfactant addition. Improved polymer hydration may enhance the effectiveness of the enzyme treatment. Therefore, the addition of surfactnt to a high caustic enzyme hydration brine or to hydration brine with just enzyme will also be beneficial.

While certain embodiments and details have been shown for the purpose of illustrating this invention, it will be apparent to those skilled in this art that various changes and modifications may be made herein without departing from the spirit or the scope of the invention.

I claim:

1. In an improved hydrocarbon recovery process wherein subterranean petroliferous formations are flooded with aqueous mixtures of biopolymers to increase hydrocarbon recovery, said polymer being treated with enzymes to solubilize cell debris prior to filtration, the improvement comprising treating the polymer, prior to filtration in use in a petroliferous formation with a specific bacillis enzyme at a pH of 12.5 to 13.0 to improve filterability, then filtering prior to use.

2. A method as described in claim 1 wherein the caustic/enzyme treatment is carried out at a temperature of from about 75° F. to about 120° F.

3. A method as described in claim 2 wherein the enzyme is added to the biopolymer at a concentration of from about 2½ percent to about 10 percent by weight.

4. A method as described in claim 3 wherein the filtration prior to injection is done using diatomaceous earth filters.

* * * * *

UNITED STATES PATENT AND TRADEMARK OFFICE
CERTIFICATE OF CORRECTION

PATENT NO. : 4,165,257
DATED : August 21, 1979
INVENTOR(S) : Olaf M. Stokke

It is certified that error appears in the above-identified patent and that said Letters Patent are hereby corrected as shown below:

Table 1, under subtitle Filtrate cps, second occurrence, "234" should be --2.34--.

Table 1, under subtitle Filtrate cps, second occurrence, "202" should be --2.02--.

Signed and Sealed this

Thirteenth Day of November 1979

[SEAL]

Attest:

RUTH C. MASON
Attesting Officer

LUTRELLE F. PARKER
Acting Commissioner of Patents and Trademarks